United States Patent
Murakita

(10) Patent No.: US 12,303,098 B2
(45) Date of Patent: *May 20, 2025

(54) IMAGE PROCESSING DEVICE, IMAGE PROCESSING METHOD, AND IMAGE PROCESSING SYSTEM

(71) Applicant: SONY GROUP CORPORATION, Tokyo (JP)

(72) Inventor: Masashi Murakita, Chiba (JP)

(73) Assignee: SONY GROUP CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 18/356,284

(22) Filed: Jul. 21, 2023

(65) Prior Publication Data
US 2023/0363620 A1 Nov. 16, 2023

Related U.S. Application Data

(63) Continuation of application No. 17/567,389, filed on Jan. 3, 2022, now Pat. No. 11,737,647, which is a (Continued)

(30) Foreign Application Priority Data

Feb. 12, 2015 (JP) .................................. 2015-025133

(51) Int. Cl.
*A61B 1/00* (2006.01)
*A61B 1/045* (2006.01)
(Continued)

(52) U.S. Cl.
CPC ........ *A61B 1/000095* (2022.02); *A61B 1/045* (2013.01); *A61B 1/0655* (2022.02);
(Continued)

(58) Field of Classification Search
CPC . A61B 1/000095; A61B 1/045; A61B 1/0655; A61B 1/0669; G02B 23/24;
(Continued)

(56) References Cited

U.S. PATENT DOCUMENTS 10,623,651 B2 * 4/2020 Murakita ............... H04N 23/56
11,228,718 B2 * 1/2022 Murakita ......... A61B 1/000095
(Continued)

FOREIGN PATENT DOCUMENTS

| JP | 07-194528 A | 8/1995 |
| JP | 08-211306 A | 8/1996 |

(Continued)

OTHER PUBLICATIONS

Office Action for JP Patent Application No. 2020-092701, issued on May 11, 2021, 03 pages of English Translation and 03 pages of Office Action.

(Continued)

*Primary Examiner* — Girumsew Wendmagegn
(74) *Attorney, Agent, or Firm* — CHIP LAW GROUP

(57) ABSTRACT

It is desirable to provide a technology capable of further appropriately adjusting the luminance of the endoscopic image. Provided is an image processing device including: an area extraction unit configured to extract, as an extraction area, an area corresponding to the size of an insertion unit from an endoscopic image based on imaging by an image sensor; and an exposure control unit configured to perform exposure control on a basis of an output value of the image sensor in the extraction area.

12 Claims, 7 Drawing Sheets

Related U.S. Application Data continuation of application No. 16/823,848, filed on Mar. 19, 2020, now Pat. No. 11,228,718, which is a continuation of application No. 15/546,111, filed as application No. PCT/JP2015/082324 on Nov. 17, 2015, now Pat. No. 10,623,651.

(51) Int. Cl.

| | | |
|---|---|---|
| A61B 1/06 | (2006.01) | |
| G02B 23/24 | (2006.01) | |
| G06T 7/60 | (2017.01) | |
| H04N 7/18 | (2006.01) | |
| H04N 23/56 | (2023.01) | |
| H04N 23/71 | (2023.01) | |
| H04N 23/72 | (2023.01) | |
| H04N 23/73 | (2023.01) | |
| H04N 23/74 | (2023.01) | |
| H04N 23/12 | (2023.01) | |
| H04N 23/50 | (2023.01) | |
| H04N 23/63 | (2023.01) | |

(52) U.S. Cl.
CPC ............... *G02B 23/24* (2013.01); *G06T 7/60* (2013.01); *H04N 7/183* (2013.01); *H04N 23/56* (2023.01); *H04N 23/71* (2023.01); *H04N 23/72* (2023.01); *H04N 23/73* (2023.01); *H04N 23/74* (2023.01); *A61B 1/0669* (2013.01); *G06T 2207/10024* (2013.01); *G06T 2207/10068* (2013.01); *H04N 23/12* (2023.01); *H04N 23/555* (2023.01); *H04N 23/63* (2023.01)

(58) Field of Classification Search
CPC ............. G06T 7/60; G06T 2207/10024; G06T 2207/10068; H04N 7/183; H04N 23/56; H04N 23/71; H04N 23/72; H04N 23/73; H04N 23/74; H04N 23/12; H04N 23/555; H04N 23/63

See application file for complete search history.

(56) References Cited

U.S. PATENT DOCUMENTS

| | | | | |
|---|---|---|---|---|
| 11,737,647 | B2* | 8/2023 | Murakita | ............... H04N 23/74 348/68 |
| 2003/0076411 | A1* | 4/2003 | Lida | ....................... H04N 7/183 348/E7.087 |
| 2004/0092792 | A1 | 5/2004 | Kobayashi | |
| 2004/0116775 | A1 | 6/2004 | Taniguchi et al. | |
| 2010/0048993 | A1 | 2/2010 | Shidara | |
| 2014/0371535 | A1 | 12/2014 | Seto | |

FOREIGN PATENT DOCUMENTS

| | | |
|---|---|---|
| JP | 08-336160 A | 12/1996 |
| JP | 2000-287202 A | 10/2000 |
| JP | 2002-263064 A | 9/2002 |
| JP | 2003-180631 A | 7/2003 |
| JP | 2004-147924 A | 5/2004 |
| JP | 2005-006856 A | 1/2005 |
| JP | 2005-131129 A | 5/2005 |
| JP | 2005-279253 A | 10/2005 |
| JP | 2009-519764 A | 5/2009 |
| JP | 2010-000183 A | 1/2010 |
| JP | 2013-042998 A | 3/2013 |

OTHER PUBLICATIONS

International Search Report and Written Opinion of PCT Application No. PCT/JP2015/082324, issued on Feb. 9, 2016, 02 pages of English Translation and 07 pages of ISRWO.

Office Action for JP Patent Application No. 2016-574627, issued on Feb. 12, 2020, 07 pages of Office Action and 07 pages of English Translation.

Notice of Allowance for U.S. Appl. No. 15/546,111, issued on Dec. 13, 2019, 09 pages.

Non-Final Office Action for U.S. Appl. No. 15/546,111, issued on Jul. 25, 2019, 15 pages.

Final Office Action for U.S. Appl. No. 15/546,111, issued on Apr. 18, 2019, 16 pages.

Office Action for JP Patent Application No. 2016-574627, issued on Aug. 6, 2019, 03 pages of Office Action and 02 Pages of English Translation.

Non-Final Office Action for U.S. Appl. No. 15/546,111, issued on Oct. 18, 2018,18 pages.

International Preliminary Report on Patentability of PCT Application No. PCT/JP2015/082324, issued on Aug. 24, 2017, 7 pages of English Translation and 04 pages of IPRP.

Notice of Allowance for U.S. Appl. No. 16/823,848 issued on Sep. 17, 2021, 09 pages.

Non-Final Office Action for U.S. Appl. No. 16/823,848, issued on Feb. 4, 2021, 9 pages.

Final Office Action for U.S. Appl. No. 16/823,848, issued on Jul. 6, 2021, 13 pages.

Notice of Allowance for U.S. Appl. No. 17/567,389 issued on Jul. 19, 2023, 02 pages.

Notice of Allowance for U.S. Appl. No. 17/567,389 issued on Apr. 17, 2023, 09 pages.

\* cited by examiner

Mp

IMAGE PROCESSING DEVICE, IMAGE PROCESSING METHOD, AND IMAGE PROCESSING SYSTEM

CROSS REFERENCE TO RELATED APPLICATIONS

The present application is a continuation application of U.S. patent application Ser. No. 17/567,389, filed Jan. 3, 2022 which is a continuation application of U.S. patent application Ser. No. 16/823,848, filed Mar. 19, 2020, now U.S. Pat. No. 11,228,718, which is a continuation application of U.S. patent application Ser. No. 15/546,111, filed Jul. 25, 2017, now U.S. Pat. No. 10,623,651, which is a national stage entry of PCT/JP2015/082324 filed Nov. 17, 2015, which claims priority from prior Japanese Priority Patent Application JP 2015-025133 filed in the Japan Patent Office on Feb. 12, 2015, the entire content of which is hereby incorporated by reference.

TECHNICAL FIELD

The present disclosure relates to an information processing device, an information processing method, a program and an image processing system.

BACKGROUND ART

In recent years, image processing devices for processing an endoscopic image based on imaging by an image sensor have gained in popularity (e.g., see Patent Literature 1). Meanwhile, a phenomenon may occur in which the endoscopic image is partially darkened by light shielding caused by, for example, the hood of the lens for transmitting light to the image sensor. Hereinafter, such an area darkened by light shielding in the endoscopic image is also simply referred to as "black area". Moreover, a phenomenon in which such a black area occurs in the endoscopic image is also called "vignetting".

CITATION LIST

Patent Literature

Patent Literature 1:
JP 2013-42998A

DISCLOSURE OF INVENTION

Technical Problem

Here, due to the occurrence of the black area in the endoscopic image, there is a case where exposure control may be performed so that the luminance of the endoscopic image becomes excessively high. Thus, an area other than the black area (hereinafter, also referred to as "observation area") may become excessively bright. Accordingly, it is desirable to provide a technology capable of further appropriately adjusting the luminance of the endoscopic image.

Solution to Problem

According to the present disclosure, there is provided an image processing device including: an area extraction unit configured to extract, as an extraction area, an area corresponding to the size of an insertion unit from an endoscopic image based on imaging by an image sensor; and an exposure control unit configured to perform exposure control on a basis of an output value of the image sensor in the extraction area.

According to the present disclosure, there is provided an image processing device including: extracting, as an extraction area, an area corresponding to the size of an insertion unit from an endoscopic image based on imaging by an image sensor; and performing exposure control by a processor on a basis of an output value of the image sensor in the extraction area.

According to the present disclosure, there is provided a program for causing a computer to function as an image processing device including: an area extraction unit configured to extract, as an extraction area, an area corresponding to the size of an insertion unit from an endoscopic image based on imaging by an image sensor; and an exposure control unit configured to perform exposure control on a basis of an output value of the image sensor in the extraction area.

According to the present disclosure, there is provided an image processing system including: a light source unit configured to emit light; an image sensor configured to capture an endoscopic image by receiving reflected light of the light emitted by the light source unit; and an image processing device including an area extraction unit configured to extract, as an extraction area, an area corresponding to the size of an insertion unit from the endoscopic image, and an exposure control unit configured to perform exposure control on a basis of an output value of the image sensor in the extraction area.

Advantageous Effects of Invention

As described above, according to the present disclosure, a technology capable of further appropriately adjusting luminance of an endoscopic image is provided. Note that the effects described above are not necessarily limitative. With or in the place of the above effects, there may be achieved any one of the effects described in this specification or other effects that may be grasped from this specification.

MODE(S) FOR CARRYING OUT THE INVENTION

Figure 1:
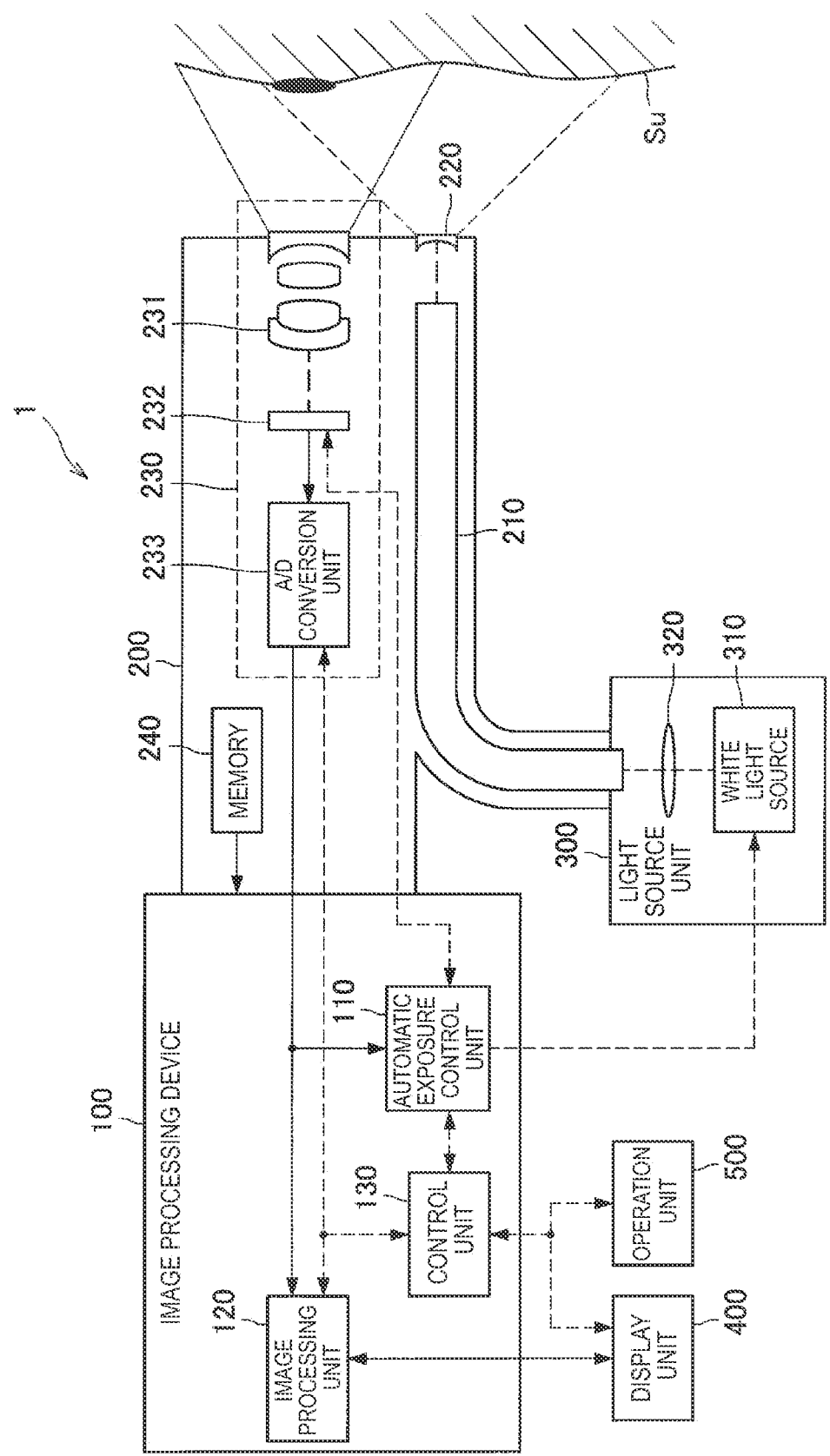
FIG. 1 is a diagram showing an exemplary configuration of an image processing system according to an embodiment of the present disclosure.

Hereinafter, (a) preferred embodiment(s) of the present disclosure will be described in detail with reference to the appended drawings. In this specification and the appended drawings, structural elements that have substantially the same function and structure are denoted with the same reference numerals, and repeated explanation of these structural elements is omitted.

Note that, in this description and the drawings, structural elements that have substantially the same function and structure are sometimes distinguished from each other using different alphabets after the same reference sign. However, when there is no need in particular to distinguish structural elements that have substantially the same function and structure, the same reference sign alone is attached.

Note that description will be given in the following order.
1. Embodiment of the present disclosure
1.1. Exemplary system configuration
1.2. Exemplary function configuration
1.3. Functional detail of automatic exposure control unit
2. Conclusion

1. Embodiment of the Present Disclosure

[1.1. Exemplary System Configuration]

First, an exemplary configuration of an image processing system according to an embodiment of the present disclosure will be described with reference to the drawings. FIG. 1 is a diagram showing an exemplary configuration of an image processing system according to an embodiment of the present disclosure. As shown in FIG. 1, the image processing system 1 includes an image processing device 100, an insertion unit 200, a light source unit 300, a display unit 400, and an operation unit 500.

The light source unit 300 includes a white light source 310 and a condenser lens 320. The white light source 310 emits white light. Note that this specification mainly describes examples of using white light, but the color of light is not limited in particular. Accordingly, instead of the white light source 310, light sources which emit visible light other than white may be used (e.g., instead of the white light source 310, RGB lasers which can perform variable control of RGB output may be used). The condenser lens 320 focuses the light emitted by the white light source 310 to a light guide 210 described below.

The insertion unit 200 can correspond to a scope to be inserted into a body. Specifically, the insertion unit 200 may be a rigid endoscope or a soft endoscope. The insertion unit 200 includes the light guide 210, an illumination lens 220, an imaging unit 230, and a memory 240. The imaging unit 230 includes an objective lens 231, an image sensor (imaging element) 232, and an A/D (analog/digital) conversion unit 233. The light guide 210 guides the light focused by the light source unit 300 to the end of the insertion unit 200. The illumination lens 220 diffuses the light that has been guided to the end by the light guide 210, and irradiates an observation target (subject Su) with the diffused light. The objective lens 231 focuses the reflected light returning from the observation target (subject Su) to form an image on the image sensor 232. The image sensor 232 outputs analog signals (endoscopic image) captured by receiving the reflected light to the A/D conversion unit 233.

Note that the image sensor 232 has, for example, a primary color Bayer array. In such a case, the endoscopic image obtained by the image sensor 232 is a primary color Bayer image. The primary color Bayer image is an image in which each pixel has any of R, G, and B signals, and the RGB pixels are arranged in a staggered pattern. However, the image sensor 232 is not limited to the primary color Bayer array. Namely, the endoscopic image is not limited to the primary color Bayer image. For example, the endoscopic image may be an image acquired by an endoscope imaging method e.g., complementary-color method or frame-sequential imaging method other than the primary color Bayer.

The A/D conversion unit 233 converts, on the basis of a control signal output from a control unit 130 described below, analog signals (endoscopic image) output from the image sensor 232 into digital signals, and outputs the digital signals (endoscopic image) to the image processing device 100. The memory 240 stores a program for implementing function of the image processing device 100 when being executed by an operation device (not shown).

Note that in the following description, the insertion unit 200 may be referred to as "scope" as appropriate. A different scope can be used for endoscopic diagnosis depending on a diagnosis region. An identification number for specifying a target diagnosis region and a function, such as a zoom function, is assigned to each scope, and in this specification, the identification number may be referred to as "scope ID". The memory 240 stores the scope ID.

The image processing device 100 includes an automatic exposure control unit 110, an image processing unit 120, and the control unit 130. The endoscopic image acquired by the imaging unit 230 is output to the automatic exposure control unit 110 and the image processing unit 120. The automatic exposure control unit 110 is connected to the white light source 310 and the image sensor 232, and controls the white light source 310 and the image sensor 232. The image processing unit 120 is connected to the display unit 400. The control unit 130 is bidirectionally connected to the imaging unit 230, the image processing unit 120, the display unit 400, and the operation unit 500, and controls these components.

The automatic exposure control unit 110 automatically performs exposure control of the image sensor 232 such that the luminance of the endoscopic image acquired by the imaging unit 230 is a value appropriate for observation (hereinafter, referred to as "appropriate value"). The automatic exposure control unit 110 will be described in detail below. The image processing unit 120 performs image processing on the endoscopic image captured by the imaging unit 230. The image processing unit 120 performs, for example, a tone transformation process and a noise reduction process. The image processing unit 120 outputs the image subjected to the image processing to the display unit 400.

The control unit 130 is connected to the imaging unit 230, the image processing unit 120, the display unit 400, and the operation unit 500, and outputs control signals for controlling these. The display unit 400 outputs the endoscopic image output by the image processing unit 120 to an image display device such as an endoscope monitor. The operation unit 500 is an interface for receiving operations from a user. For example, the operation unit 500 includes a power switch for turning ON/OFF the power supply, a shutter button for starting an imaging operation, a mode switch button for switching an imaging mode and other various modes, and the like. The exemplary configuration of the image processing system 1 according to the embodiment of the present disclosure has been described above.

[1.2. Example of Exposure Control]

Figure 2:
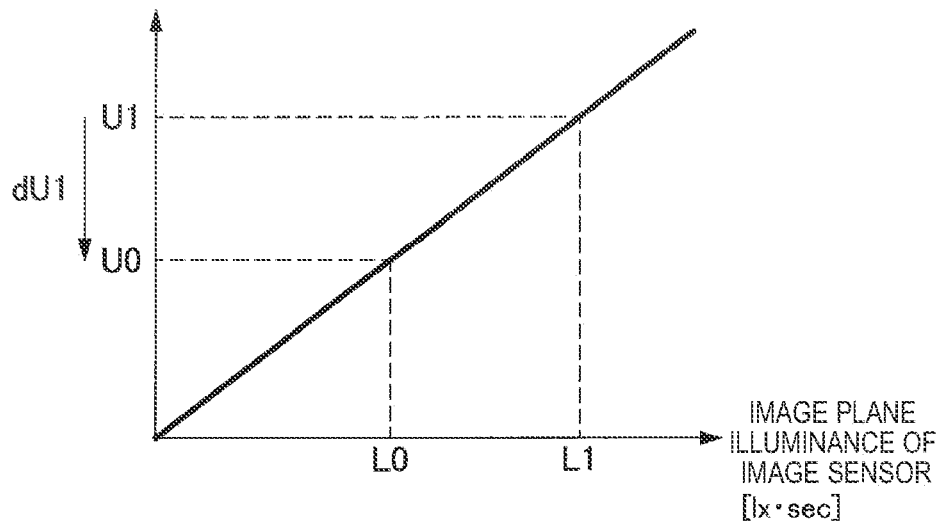
FIG. 2 is an explanatory graph of the specific example of exposure control.
Figure 3:
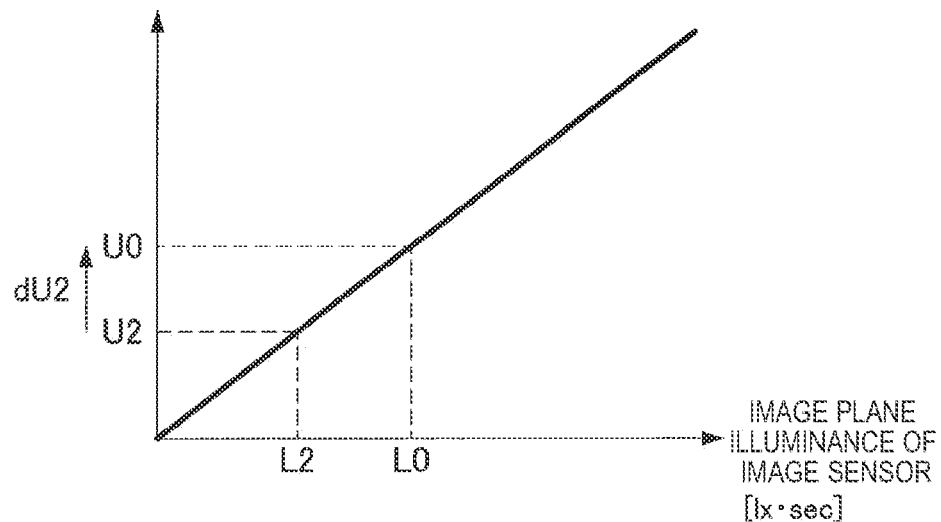
FIG. 3 is an explanatory graph of the specific example of exposure control.

Subsequently, specific examples of exposure control by the automatic exposure control unit 110 will be described. FIGS. 2 and 3 are explanatory graphs of specific examples of the exposure control. As described above, analog signals captured by the image sensor 232 are converted to digital signals (endoscopic image) by the A/D conversion unit 233. In FIGS. 2 and 3, the output value from the image sensor 232 is shown on the vertical axis. Moreover, the image plane illuminance of the image sensor 232 corresponding to each output value is shown on the horizontal axis. Note that the output value from the image sensor 232 may be a mean value of output values corresponding to each pixel.

Moreover, with reference to FIG. 2, an appropriate value of the output value from the image sensor 232 is shown as "U0", and the image plane illuminance of the image sensor 232 corresponding to the appropriate value U0 is shown as "L0". As shown in FIG. 2, for example, it is assumed that the output value U1 from the image sensor 232 is larger than the appropriate value U0. In such a case, the automatic exposure control unit 110 performs exposure control so as to decrease the output value from the image sensor 232 by dU1 (U1−U0=dU1).

On the other hand, with reference to FIG. 3, as in FIG. 2, the appropriate value of the output value from the image sensor 232 is shown as "U0", and the image plane illuminance of the image sensor 232 corresponding to the appropriate value U0 is shown as "L0". As shown in FIG. 3, for example, it is assumed that the output value U2 from the image sensor 232 is smaller than the appropriate value U0. In such a case, the automatic exposure control unit 110 performs exposure control so as to increase the output value from the image sensor 232 by dU2 (U0−U2=dU2).

For example, the exposure control may be performed by adjusting parameters for controlling exposure. A variety of parameters are assumed as the parameter for controlling exposure. For example, the parameter for controlling exposure may include at least any one of an electronic shutter speed of the image sensor 232 and a gain by which the analog signals captured by the image sensor 232 are multiplied. Alternatively, the parameter for controlling exposure may include brightness of the white light source 310 (alternatively, when an RGB laser is used instead of the white light source 310, the exposure control may be performed through light source control by modifying outputs of respective RGB).

For example, the exposure control to decrease the output value from the image sensor 232 by dU1 as shown in FIG. 2 may be executed by increasing the electronic shutter speed by an amount corresponding to dU1, or may be executed by decreasing a gain by which the analog signals captured by the image sensor 232 are multiplied by an amount corresponding to dU1. Alternatively, the exposure control to decrease the output value from the image sensor 232 may be executed by weakening the brightness of the white light source 310 by an amount corresponding to dU1.

On the other hand, the exposure control to increase the output value from the image sensor 232 by dU2 as shown in FIG. 3 may be executed by decreasing the electronic shutter speed by an amount corresponding to dU2, or may be executed by increasing a gain by which the analog signals captured by the image sensor 232 are multiplied by an amount corresponding to dU2. Alternatively, the exposure control to increase the output value from the image sensor 232 may be executed by increasing the brightness of the white light source 310 by an amount corresponding to dU2.

The specific examples of the exposure control by the automatic exposure control unit 110 have been described above.

[1.3. Functional Detail of Automatic Exposure Control Unit]

Figure 4:
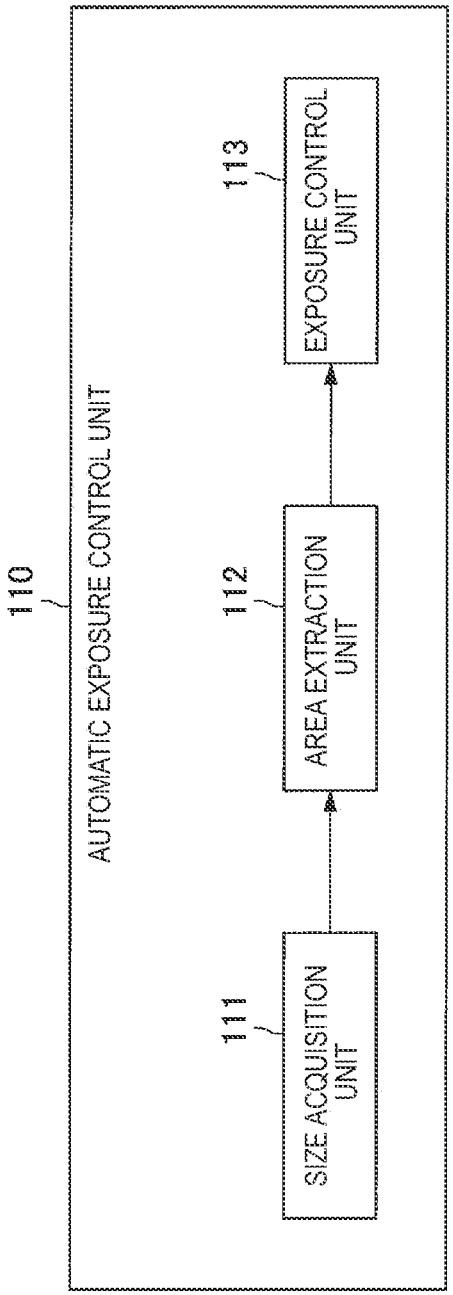
FIG. 4 is a block diagram showing an exemplary detailed functional configuration of an automatic exposure control unit.

Subsequently, detailed function of the automatic exposure control unit 110 will be described. FIG. 4 is a block diagram showing an exemplary detailed functional configuration of the automatic exposure control unit 110. As shown in FIG. 4, the automatic exposure control unit 110 includes a size acquisition unit 111, an area extraction unit 112, and an exposure control unit 112. Hereinafter, each function of the size acquisition unit 111, the area extraction unit 112 and the exposure control unit 113 will be described in detail. First, the size acquisition unit 111 acquires an endoscopic image from the imaging unit 230.

Figure 5:
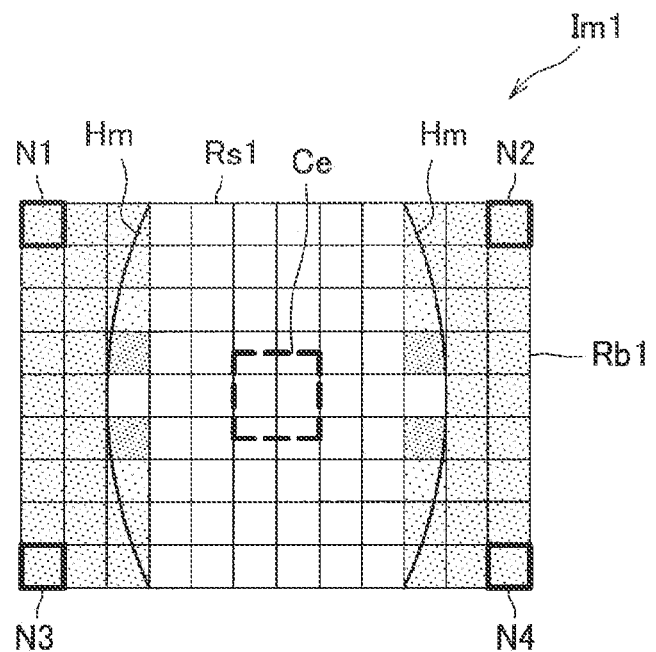
FIG. 5 is a diagram showing an exemplary endoscopic image.

FIG. 5 is a diagram showing an exemplary endoscopic image. As shown in FIG. 5, in an endoscopic image Im1, each pixel is arranged in a lattice shape. Here, as mentioned above, a phenomenon may occur in which the endoscopic image Im1 is partially darkened by light shielding caused by, for example, the hood of the lens for transmitting light to the image sensor 232. Therefore, in the endoscopic image Im1, there is a black area Rb1 in addition to an observation area Rs1. Lines Hm indicate boundary lines between the black areas Rb1 and the observation area Rs1. The color density of each pixel represents the height of the luminance of each pixel.

Here, there is a case where, due to the occurrence of the black area Rb1 in the endoscopic image Im1, exposure control may be performed by the automatic exposure control unit 110 so that the luminance of the endoscopic image Im1 becomes excessively high. Thus, the observation area Rs1 may become excessively bright. Accordingly, a technology will be described below which is capable of further appropriately adjusting the luminance of the endoscopic image Im1 by reducing the possibility that the observation area Rs1 becomes excessively bright.

Specifically, the area extraction unit 112 extracts, as an extraction area, an area corresponding to the size of the insertion unit 200 from the endoscopic image Im1 based on imaging by the image sensor 232. Then, the exposure control unit 113 performs exposure control on the basis of an output value of the image sensor in the extraction area. That makes it possible to further appropriately adjust the luminance of the endoscopic image Im1 by reducing the possibility that the observation area Rs1 becomes excessively bright.

For example, in the case of having determined that the shadow of the insertion unit 200 is imaged in the endoscopic image Im1, the exposure control unit 113 may perform exposure control based on an output value of the image sensor in the extraction area. More specifically, in the case of having determined that the shadow of the insertion unit 200 is imaged in the endoscopic image Im1, the exposure control unit 113 may adjust parameters for controlling exposure on the basis of an output value of the image sensor in the extraction area.

On the other hand, in the case of having determined that the shadow of the insertion unit 200 is not imaged in the endoscopic image Im1, the exposure control unit 113 may perform exposure control based on an output value of the image sensor in the entire endoscopic image Im1. Note that determination of whether or not the shadow of the insertion unit 200 is imaged in the endoscopic image Im1 may be made in any way.

For example, in the case that the luminance difference between the center area Ce and peripheral areas N1 to N4 is greater than a first threshold, the exposure control unit 113 may determine that the shadow of the insertion unit 200 is imaged in the endoscopic image Im1. Moreover, in the case that the luminance difference between the center area Ce and the peripheral areas N1 to N4 is less than the first threshold, the exposure control unit 113 may determine that the shadow of the insertion unit 200 is not imaged in the endoscopic image Im1. In the case that the luminance difference between the center area Ce and the peripheral areas N1 to N4 is equal to the first threshold, the exposure control unit 113 may determine it as either case.

Alternatively, the exposure control unit 113 detects a first peak and a second peak in sequence from the lower luminance side from the number-of-pixel distribution for each luminance of the endoscopic image, and then in the case that the luminance difference between the first peak and the second peak exceeds an upper limit value, the exposure control unit 113 may determine that the shadow of the insertion unit 200 is imaged in endoscopic image Im1. Moreover, in the case that the luminance difference between the first peak and the second peak does not exceed the upper limit value, the exposure control unit 113 may determine that the shadow of the insertion unit 200 is not imaged in the endoscopic image Im1.

Figure 6:
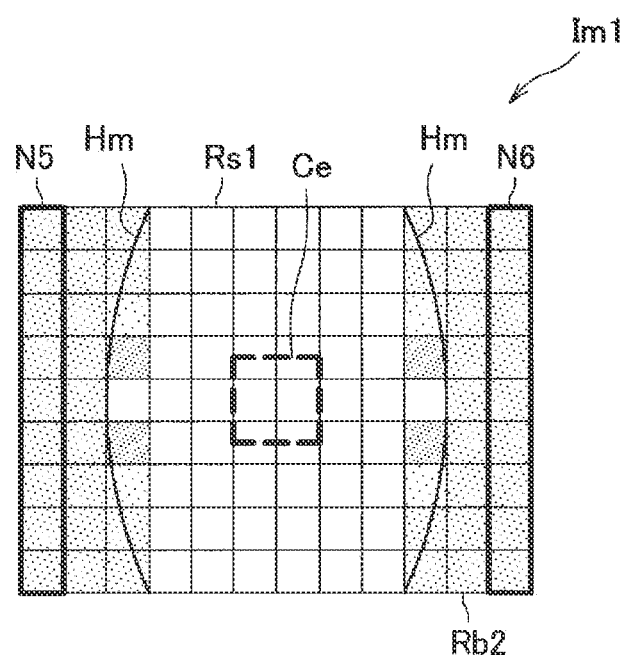
FIG. 6 is a diagram showing another exemplary peripheral area.

In the example shown in FIG. 5, the luminance of the center area Ce is assumed to use the average luminance of the four pixels present in the center of the endoscopic image Im1, but the position of the center area Ce and the number of pixels are not limited. Similarly, the luminance of the peripheral areas N1 to N4 is assumed to use the average luminance of the four pixels in the four corners of the endoscopic image Im1, but the position of the peripheral areas N1 to N4 and the number of pixels are not limited. FIG. 6 is a diagram showing another example of the peripheral area. As shown in FIG. 6, instead of the peripheral areas N1 to N4, the pixel columns present at the outermost sides of the endoscopic image Im1 may be used as peripheral areas N5 and N6.

Subsequently, the size acquisition unit 111 acquires the size of the insertion unit 200. Note that in the following description, a scope diameter (diameter of the insertion unit 200) is used as the size of the insertion unit 200, but instead of the scope diameter, other lengths of the insertion unit 200 (e.g., radius of the insertion unit 200 or the like) may be used. The size acquisition unit 111 may acquire the scope diameter from a predetermined place. For example, the size acquisition unit 111 may acquire the scope diameter (or, scope information including the scope diameter) by communicating with a scope body or external devices. Alternatively, the size acquisition unit 111 may acquire the scope diameter by calculation on the basis of the endoscopic image Im1.

The method of acquiring the scope diameter by calculation is not limited in particular. For example, in the case of scanning from a first start position of the endoscopic image Im1 toward a first target position in a first scanning direction, the size acquisition unit 111 may calculate the scope diameter on the basis of a first pixel position at which the magnitude relation between the luminance and the second threshold is first switched. At this time, the size acquisition unit 111 may calculate twice the first distance between the first pixel position and the center position as the scope diameter.

Note that the second threshold may be a fixed value, but may be set to a value depending on a situation of the endoscopic image Im1. For example, the size acquisition unit 111 may set the second threshold on the basis of a number-of-pixel distribution for each luminance of the endoscopic image Im1. More specifically, the size acquisition unit 111 may specify a median value of a number-of-pixel distribution for each luminance of the endoscopic image Im1 and set the median value as the second threshold.

Figure 7:
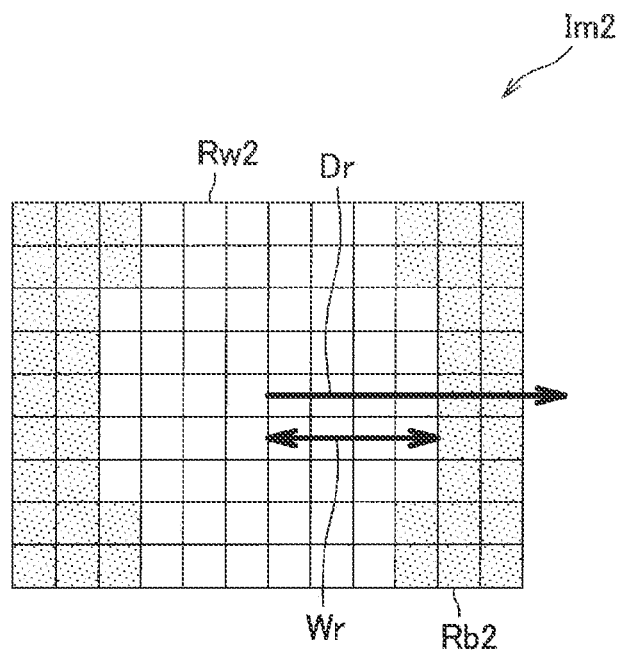
FIG. 7 is an explanatory diagram of a calculation example of a scope diameter in a case that two directions are used as the scanning direction.
Figure 8:
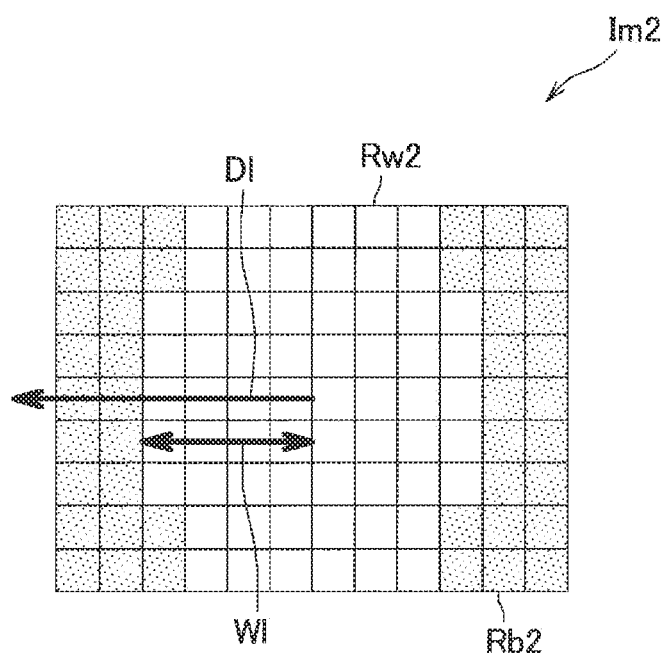
FIG. 8 is an explanatory diagram of a calculation example of the scope diameter in the case that two directions are used as the scanning direction.

Moreover, the scanning direction may be plural. The example where two directions are used as the scanning direction will be described. FIGS. 7 and 8 are explanatory diagrams of a calculation example of the scope diameter in the case where two directions are used as the scanning direction. As shown in FIG. 7, in the case of scanning from the first start position of the endoscopic image Im1 in the first scanning direction Dr, the size acquisition unit 111 calculates a first pixel position at which the magnitude relation between the luminance and the second threshold is first switched.

Moreover, as shown in FIG. 8, in the case of scanning from the second start position of the endoscopic image Im1 in the second scanning direction Dl, the size acquisition unit 111 calculates a second pixel position at which the magnitude relation between the luminance and the second threshold is first switched. Then, the size acquisition unit 111 calculates the scope diameter on the basis of the first pixel position and the second pixel position.

More specifically, in the case that a difference between a first distance Wr between the first pixel position and the center position and a second distance Wl between the second pixel position and the center position is less than a third threshold (predetermined distance), the size acquisition unit 111 may calculate a sum of the first distance Wr and the second distance Wl as the scope diameter. On the other hand, in the case that the difference between the first distance Wr and the second distance Wl is greater than the third threshold, the size acquisition unit 111 may calculate twice the larger one of the first distance Wr and the second distance Wl as the scope diameter.

As shown in FIG. 7, the first start position may be a center position of the endoscopic image Im1, and the first target position may be an end position of the endoscopic image Im1. Moreover, as shown in FIG. 8, the second start position may be also the center position of the endoscopic image Im1, and the second target position may be an end position of the endoscopic image Im1. Since a subject Su is likely to appear with high luminance inside the endoscopic image Im1, in the case that the endoscopic image Im1 is scanned from the inside toward the outside, more accurate calculation can be done.

However, the first start position, the second start position, the first target position and the second target position are not limited to the examples shown in FIGS. 7 and 8. For example, the first start position may be the end position of the endoscopic image Im1, and the first target position may be the center position of the endoscopic image Im1. Since the black area is likely to be present only at the end of the endoscopic image Im1, in the case that the endoscopic image Im1 is scanned from the outside to the inside, the calculation can be completed earlier.

Note that in the example mentioned above, the first scanning direction is the right direction and the second scanning direction is the left direction, but the first scanning direction and the second scanning direction are not limited to such an example. For example, one of the first scanning direction and the second scanning direction may be an upward direction, and the other may be a downward direction. Moreover, one of the first scanning direction and the second scanning direction may be an oblique direction (a direction from the upper right to the lower left, or a direction from the lower left to the upper right) and the other may be an oblique direction (a direction from the upper left to the lower right, or a direction from the lower right to the upper left).

Figure 9:
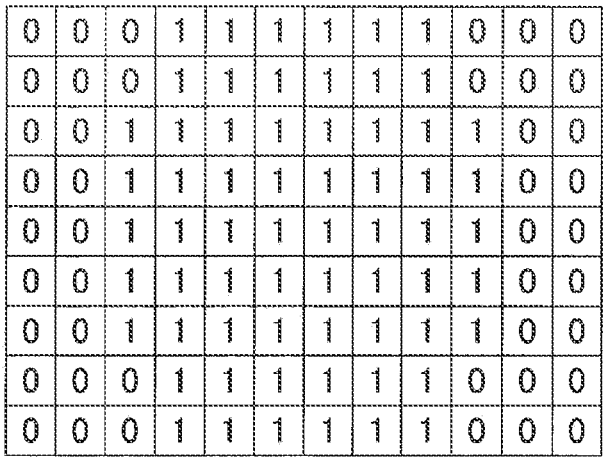
FIG. 9 is a diagram showing an exemplary black area frame map.

When the size acquisition unit 111 acquires the scope diameter, the area extraction unit 112 extracts, as an extraction area, an area corresponding to the scope diameter. For example, in the case that a map that defines the areas to be extracted (hereinafter, also referred to as "black area frame map") is associated in advance with the scope diameter, the area extraction unit 112 acquires the black area frame map corresponding to the scope diameter acquired by the size acquisition unit 111. FIG. 9 is a diagram showing an exemplary black area frame map. With reference to FIG. 9, in the black area frame map Mp, the areas to be extracted are shown as "1" and the areas to be excluded are shown as "0".

The area extraction unit 112 extracts pixels set as the area to be extracted in the black area frame map Mp from the endoscopic image Im1. FIGS. 7 and 8 show the extraction area Rw2 and the excluded area Rb2. The exposure control unit 113 then performs exposure control on the basis of an output value of the image sensor in the extraction area extracted by the area extraction unit 112. Note that the output value from the image sensor 232 in the extraction area may be a mean value of the output values corresponding to each pixel of the extraction area. It is thereby possible to further appropriately adjust the luminance of the endoscopic image Im1 by reducing a possibility that the observation area Rs1 becomes excessively bright.

Figure 10:
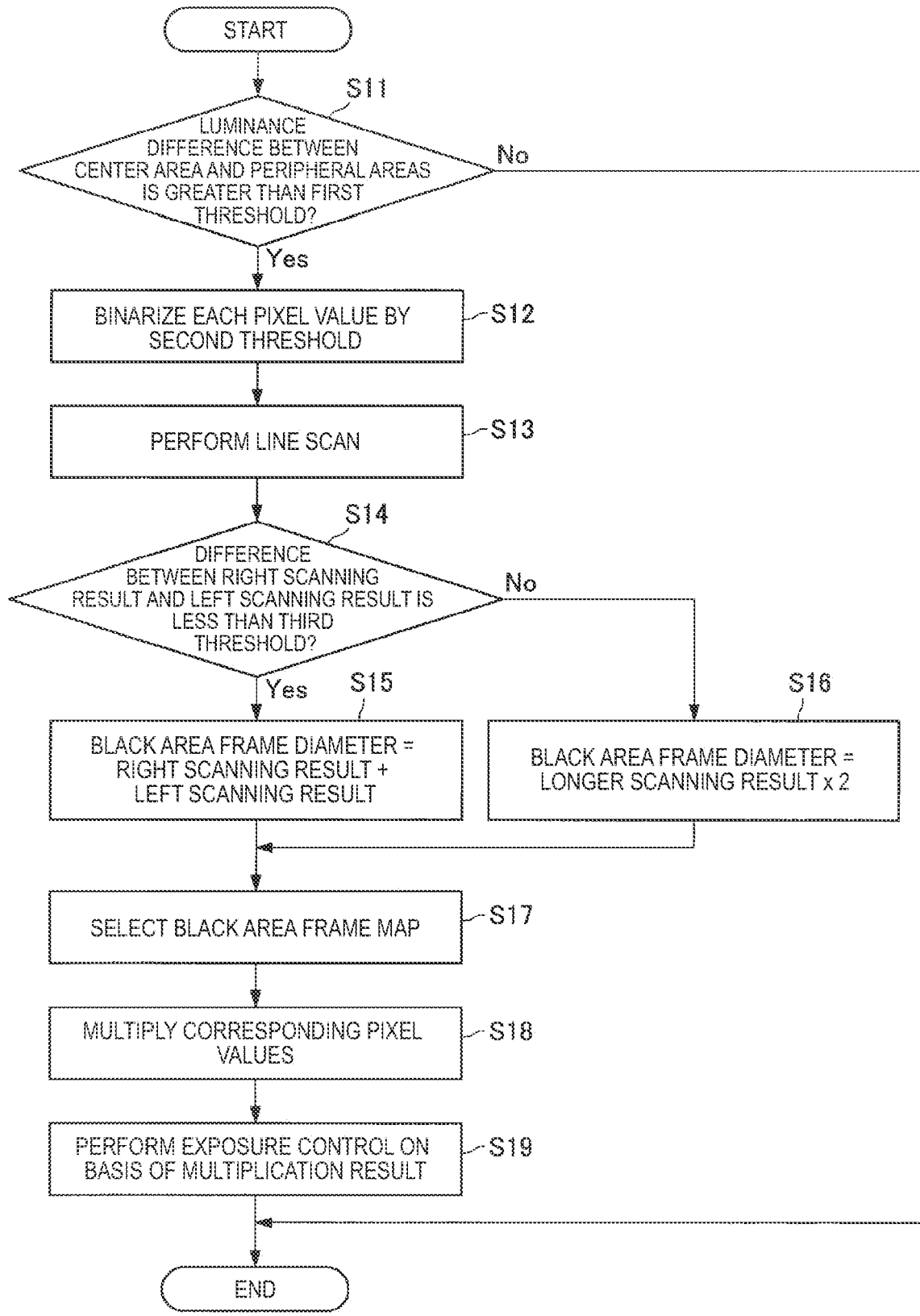
FIG. 10 is a flowchart showing an exemplary operation of exposure control depending on the scope diameter.

Subsequently, an exemplary operation of the size acquisition unit 111, the area extraction unit 112 and the exposure control unit 113 as described above will be described. FIG. 10 is a flowchart showing an exemplary operation of exposure control depending on the scope diameter. Note that the exemplary operation shown in FIG. 10 is a flowchart showing an exemplary operation of exposure control depending on the scope diameter. Accordingly, the operation of exposure control depending on the scope diameter is not limited to the exemplary operation shown in FIG. 10. Note that FIG. 10 shows the scope diameter as a black area frame diameter.

As shown in FIG. 10, in the case that the luminance difference between the center area Ce and the peripheral areas N1 to N4 (or N5, N6) is less than the first threshold in the endoscopic image Im1 ("No" in S11), the area extraction unit 112 ends the operation. On the other hand, in the case that the luminance difference between the center area Ce and the peripheral areas N1 to N4 (or N5, N6) is greater than the first threshold in the endoscopic image Im1 ("Yes" in S11), the area extraction unit 112 binarizes each pixel of the endoscopic image Im1 by the second threshold (S12).

Subsequently, the area extraction unit 112 performs line scan on the binarized image (S13). Here, in the case that a difference between a scanning result in the right direction (hereinafter, also referred to as "right scanning result") and a scanning result in the left direction (hereinafter, also referred to as "left scanning result") is greater than the third threshold ("Yes" in S14), the area extraction unit 112 sets the sum of the right scanning result and the left scanning result to the black area frame diameter (S15), and the operation is shifted to S17.

On the other hand, in the case that the difference between the right scanning result and the left scanning result is less than the third threshold ("No" in S14), the area extraction unit 112 sets, to the black area frame diameter, twice the longer one of the scanning results (S16), and the operation is shifted to S17. Subsequently, the area extraction unit 112 selects the black area frame map Mp corresponding to the black area frame diameter (S17), and multiplies pixel values corresponding to the black area frame map Mp and the endoscopic image Im1 (S18). By such multiplication, an extraction area Rw2 is extracted.

Subsequently, the exposure control unit 113 performs exposure control on the basis of the multiplication result (S19). The exposure control unit 113 performs exposure control on the basis of an output value of the image sensor in the extraction area Rw2 extracted by the area extraction unit 112. It is thereby possible to further appropriately adjust the luminance of the endoscopic image Im1 by reducing a possibility that the observation area Rs1 becomes excessively bright.

The detailed function of the automatic exposure control unit 110 has been described above.

2. Conclusion

As described above, according to the embodiment of the present disclosure, the image processing device 100 is provided which includes the area extraction unit 112 configured to extract an area corresponding to the size of the insertion unit 200 as an extraction area from the endoscopic image Im1 based on imaging by the image sensor 232 and the exposure control unit 113 configured to perform exposure control on the basis of an output value of the image sensor in the extraction area. According to such a configuration, it is possible to further appropriately adjust the luminance of the endoscopic image Im1 by reducing a possibility that the observation area Rs1 becomes excessively bright.

The preferred embodiment(s) of the present disclosure has/have been described above with reference to the accompanying drawings, whilst the present disclosure is not limited to the above examples. A person skilled in the art may find various alterations and modifications within the scope of the appended claims, and it should be understood that they will naturally come under the technical scope of the present disclosure.

Further, the effects described in this specification are merely illustrative or exemplified effects, and are not limitative. That is, with or in the place of the above effects, the technology according to the present disclosure may achieve other effects that are clear to those skilled in the art from the description of this specification. Additionally, the present technology may also be configured as below.

(1)
An image processing device including:
an area extraction unit configured to extract, as an extraction area, an area corresponding to the size of an insertion unit from an endoscopic image based on imaging by an image sensor; and
an exposure control unit configured to perform exposure control on a basis of an output value of the image sensor in the extraction area.

(2)
The image processing device according to (1), including:
a size acquisition unit configured to acquire the size of the insertion unit.

(3)
The image processing device according to (2),
in which the size acquisition unit acquires the size of the insertion unit from the insertion unit.

(4)
The image processing device according to (2),
in which the size acquisition unit acquires the size of the insertion unit by calculation on a basis of the endoscopic image.

(5)
The image processing device according to (4),
in which the size acquisition unit calculates the size of the insertion unit on a basis of a first pixel position at which a magnitude relation between a luminance and a threshold is first switched, in a case of scanning from a first start position toward a first target position of the endoscopic image in a first scanning direction.

(6)
The image processing device according to (5),
in which the first start position is a center position of the endoscopic image, and the first target position is an end position of the endoscopic image.

(7)
The image processing device according to (5),
in which the first start position is an end position of the endoscopic image, and the first target position is a center position of the endoscopic image.

(8)
The image processing device according to (6) or (7),
in which the size acquisition unit calculates, as the size of the insertion unit, a first distance between the first pixel position and the center position or twice the first distance.

(9)
The image processing device according to any one of (5) to (8),
in which the first scanning direction is an upward direction, a downward direction, a left direction, a right direction or an oblique direction.

(10)
The image processing device according to (6),
in which the size acquisition unit calculates the size of the insertion unit on a basis of a second pixel position at which a magnitude relation between a luminance and a threshold is first switched and the first pixel position in a case of scanning from a second start position of the endoscopic image in a second scanning direction.

(11)
The image processing device according to (10),
in which in a case that a difference between a first distance between the first pixel position and the center position and a second distance between the second pixel position and the center position is less than a predetermined distance, the size acquisition unit calculates, as the size of the insertion unit, a sum of the first distance and the second distance.

(12)
The image processing device according to (10),
in which in a case that a difference between a first distance between the first pixel position and the center position and a second distance between the second pixel position and the center position is greater than a predetermined distance, the size acquisition unit calculates, as the size of the insertion unit, twice the larger one of the first distance and the second distance.

(13)
The image processing device according to any one of (5) to (12),
in which the size acquisition unit sets the threshold on a basis of a number-of-pixel distribution for each luminance of the endoscopic image.

(14)
The image processing device according to any one of (1) to (13),
in which the exposure control unit adjusts a parameter for controlling exposure on a basis of an output value of the image sensor in the extraction area.

(15)
The image processing device according to (14),
in which the parameter includes at least any one of an electronic shutter speed of the image sensor and a gain by which an analog signal captured by the image sensor is multiplied.

(16)
The image processing device according to any one of (14),
in which the parameter includes brightness of a light source.

(17)
The image processing device according to any one of (1) to (16),
in which the exposure control unit performs the exposure control based on an output value of the image sensor in the extraction area in a case of having determined that a shadow of the insertion unit is imaged in the endoscopic image.

(18)
An image processing device including:
extracting, as an extraction area, an area corresponding to the size of an insertion unit from an endoscopic image based on imaging by an image sensor; and
performing exposure control by a processor on a basis of an output value of the image sensor in the extraction area.

(19)
A program for causing a computer to function as an image processing device including: an area extraction unit configured to extract, as an extraction area, an area corresponding to the size of an insertion unit from an endoscopic image based on imaging by an image sensor; and
an exposure control unit configured to perform exposure control on a basis of an output value of the image sensor in the extraction area.

(20)
An image processing system including:
a light source unit configured to emit light;
an image sensor configured to capture an endoscopic image by receiving reflected light of the light emitted by the light source unit; and
an image processing device including
an area extraction unit configured to extract, as an extraction area, an area corresponding to the size of an insertion unit from the endoscopic image, and
an exposure control unit configured to perform exposure control on a basis of an output value of the image sensor in the extraction area.

REFERENCE SIGNS LIST 1 image processing system
100 image processing device
110 automatic exposure control unit
111 size acquisition unit
112 area extraction unit
112 exposure control unit
113 exposure control unit
120 image processing unit
130 control unit
200 insertion unit
210 light guide
220 illumination lens 230 imaging unit
231 objective lens
232 image sensor
240 memory
300 light source unit
310 white light source
320 condenser lens
400 display unit
500 operation unit
Ce center area
Dl second scanning direction
Dr first scanning direction
Im1 endoscopic image
Mp black area frame map
N1 to N6 peripheral areas
Rb1 black area
Rb2 excluded area
Rs1 observation area
Rw2 extraction area
Su subject
Wl second distance
Wr first distance

The invention claimed is:

1. An endoscopy system, comprising:
 circuitry configured to:
  obtain, from an endoscope, an endoscopic image including an observation area and a black area, wherein the black area is caused by vignetting process of the endoscope;
  determine an extraction area of the endoscopic image corresponding to a size of the endoscope, based on a first luminance value in a center area of the endoscopic image and a second luminance value in a peripheral area of the endoscopic image; and
  control an exposure of the endoscope based on a third luminance value in the extraction area of the endoscopic image.

2. The endoscopy system according to claim 1, wherein the circuitry is further configured to control, based on the third luminance value in the extraction area, the exposure of the endoscope for an imaging operation by an image sensor.

3. The endoscopy system according to claim 1, wherein the extraction area corresponds to a size of an optical system of an insertion unit of the endoscope.

4. The endoscopy system according to claim 3, wherein the size of the optical system of the insertion unit is a diameter of the optical system of the insertion unit.

5. The endoscopy system according to claim 3, wherein the circuitry is further configured to:
  acquire fourth luminance values from a first position of the endoscopic image to a second position of the endoscopic image; and
  determine the size of the optical system of the insertion unit based on a change in the fourth luminance values.

6. The endoscopy system according to claim 1, wherein the circuitry is further configured to determine the extraction area based on fourth luminance values of at least two regions of the endoscopic image.

7. The endoscopy system according to claim 6, the circuitry is further configured to determine the extraction area based on the fourth luminance values of the at least two regions of the endoscopic image and threshold values.

8. The endoscopy system according to claim 1, wherein the circuitry is further configured to determine the extraction area based on a luminance difference between at least two areas of the endoscopic image.

9. The endoscopy system according to claim 1, wherein the circuitry is further configured to adjust, based on the third luminance value in the extraction area, a parameter to control the exposure.

10. The endoscopy system according to claim 1, wherein the endoscope is one of a rigid endoscope or a flexible endoscope.

11. An image processing device, comprising:
 circuitry configured to:
  obtain, from an endoscope, an endoscopic image including an observation area and a black area, wherein the black area is caused by vignetting of the endoscope;
  determine an extraction area of the endoscopic image corresponding to a size of the endoscope, based on a first luminance value in a center area of the endoscopic image and a second luminance value in a peripheral area of the endoscopic image; and
  control an exposure of the endoscope based on a third luminance value in the extraction area of the endoscopic image.

12. An image processing method, comprising:
 obtaining, from an endoscope, an endoscopic image including an observation area and a black area, wherein the black area is caused by vignetting of the endoscope;
 determining an extraction area of the endoscopic image corresponding to a size of the endoscope, based on a first luminance value in a center area of the endoscopic image and a second luminance value in a peripheral area of the endoscopic image; and
 controlling an exposure of the endoscope based on a third luminance value in the extraction area of the endoscopic image.

* * * * *